US009610115B2

(12) United States Patent
Rothweiler et al.

(10) Patent No.: US 9,610,115 B2
(45) Date of Patent: Apr. 4, 2017

(54) RF SEALING INSTRUMENT (71) Applicant: Aesculap AG, Tuttlingen (DE)

(72) Inventors: Christoph Rothweiler, Donauschingen (DE); Patrick Heizmann, Huefingen (DE)

(73) Assignee: Aesculap AG (DE)

( * ) Notice: Subject to any disclaimer, the term of this patent is extended or adjusted under 35 U.S.C. 154(b) by 382 days.

(21) Appl. No.: 13/919,096

(22) Filed: Jun. 17, 2013

(65) Prior Publication Data

US 2013/0338660 A1    Dec. 19, 2013

(30) Foreign Application Priority Data

Jun. 18, 2012 (DE) .................. 10 2012 105 263

(51) Int. Cl.
*A61B 18/14* (2006.01)
*A61B 18/18* (2006.01)
(Continued)

(52) U.S. Cl.
CPC ...... *A61B 18/1442* (2013.01); *A61B 18/1445* (2013.01); *A61B 18/18* (2013.01);
(Continued)

(58) Field of Classification Search
CPC  A61B 2017/00393; A61B 2018/00916; A61B 2018/00922; A61B 2018/0094;
(Continued)

(56) References Cited

U.S. PATENT DOCUMENTS 5,531,744 A      7/1996 Nardella et al.
2004/0153020 A1  8/2004 Bartel et al.
                 (Continued)

FOREIGN PATENT DOCUMENTS

DE    24 55 171        8/1976
DE    102 05 093 A1    1/2003
                (Continued)

OTHER PUBLICATIONS

European Patent Office Communication issued in related European Appln. No. 13168586.9, dated Sep. 11, 2014, with English language translation.

(Continued)

*Primary Examiner* — Jaymi Della
(74) *Attorney, Agent, or Firm* — RatnerPrestia (57) ABSTRACT A bipolar RF sealing instrument includes two instrument branches which are movable relative to one another at least to an open and a closed position, and an instrument handle with two handle units, each associated with a respective instrument branch and coupled for manually operating the instrument branches and for applying to the instrument branches a predetermined closing force at the closed position, a first of the two instrument branches having a terminal for an external RF generator and the second instrument branch adapted to be electrically coupled via an instrument-internal power contact with the first instrument branch. The power contact may be a spring contact for contact closure at a closure position. In addition or alternatively, an instrument-internal control switch is present and only activated when the predetermined closing force is reached, to enable the supply of electric current from an external RF generator to the instrument branch(es).

12 Claims, 5 Drawing Sheets (51) Int. Cl.
*A61B 18/00* (2006.01)
*A61B 18/12* (2006.01)
*A61B 90/00* (2016.01)

(52) U.S. Cl.
CPC ... *A61B 18/1206* (2013.01); *A61B 2018/0063* (2013.01); *A61B 2018/0094* (2013.01); *A61B 2018/00559* (2013.01); *A61B 2018/00607* (2013.01); *A61B 2018/00619* (2013.01); *A61B 2018/00708* (2013.01); *A61B 2018/00922* (2013.01); *A61B 2018/00928* (2013.01); *A61B 2018/1455* (2013.01); *A61B 2018/1497* (2013.01); *A61B 2090/031* (2016.02); *A61B 2090/061* (2016.02); *A61B 2090/065* (2016.02); *A61B 2090/0811* (2016.02)

(58) Field of Classification Search
CPC  A61B 2018/00946; A61B 2018/00952; A61B 2018/00958; A61B 2018/00928
USPC ...................................................... 606/50–52
See application file for complete search history.

(56) References Cited

U.S. PATENT DOCUMENTS

| | | |
|---|---|---|
| 2008/0215048 A1 | 9/2008 | Hafner et al. |
| 2011/0092970 A1* | 4/2011 | Alberstetter et al. ........... 606/41 |
| 2012/0083786 A1* | 4/2012 | Artale ................ A61B 18/1442 606/51 |

FOREIGN PATENT DOCUMENTS

| | | |
|---|---|---|
| DE | 10 2006 042 985 A1 | 4/2007 |
| DE | 102008032511 A1 | 12/2009 |
| EP | 2436330 A1 | 4/2012 |

OTHER PUBLICATIONS

German Search Report issued in related German Application No. 10 2012 105 263.8, mailed Jan. 30, 2013 (with partial English translation).

* cited by examiner

RF SEALING INSTRUMENT

RELATED APPLICATIONS

This application claims priority to German Application No. DE 10 2012 105 263.8, filed Jun. 18, 2012, the content of which is incorporated by reference herein in its entirety and for all purposes.

TECHNICAL FIELD

The present invention relates generally to a surgical RF bipolar instrument, and more particularly to a RF bipolar sealing instrument.

BACKGROUND

Modern surgical RF instruments of the bipolar type allow nowadays new methods as well as surgical operating techniques for a permanent and safe thermofusion of vessels and tissue structures. The high reliability achieved by these instruments in sealing processes offers a wide application spectrum also in the field of minimally invasive techniques with particularly short access paths, whereby a reduced time of operation and reduced costs of operation can be accomplished.

Thermofusion is essentially based on two mechanisms that must match with each other in the best possible way so as to obtain a good fusion result, viz.
  firstly, on the application of current via two opposed instrument branches equipped with electrodes and used for fixing therebetween the tissue to be treated, and
  secondly, on the contact pressure (clamping force) with which the tissue to be treated is compressed between the instrument branches.

Both factors influence and physically change the collagen and elastin structures and produce also the parchmenty thermofusion zone which optically indicates safe sealing of the vessels.

The fundamental surgical course of action in executing thermofusion by means of a known type of RF sealing instrument can be described uniformly for all known instruments as follows:

The tissue to be severed and sealed is first grasped with the two branches of the instrument and clamped therebetween with a defined clamping force. Subsequently, the thermofusion mode is activated via a manual switch or a foot switch, whereupon the electrodes of one branch have applied thereto an RF current, which is conducted through the clamped tissue to the electrode of the opposite branch thus thermofusing the tissue. The supply of current is stopped either manually or automatically as soon as the optimum fusion quality has been accomplished. In view of the bipolar nature of the instrument, lateral thermal damage is avoided to a large extent. Finally, the tissue is cut through in the middle of the fusion zone by means of a (mechanical or electrical) scalpel or a sharp-edged forceps constituting a further component of the instrument.

In practice, RF sealing instruments of the bipolar type are successfully used, e.g. for vaginal hysterectomy or thyroidectomy executed by minimal incision techniques. However, also in other disciplines, such as enteroanastomosis, bipolar RF sealing instruments increasingly replace known standard instruments, such as the clip suture instrument which is also referred to as stapler. In this special case, the open surgical operation technique for executing an enteroanastomosis necessitates, among other prerequisites, the divisibility of the instrument into two instrument parts that are freely movable independently of one another. When an RF sealing instrument of the bipolar type is used, the connection of the tissue parts for anastomosing is therefore not accomplished by clips, but the tissue parts are so to speak "fused" by a high-frequency current. Nevertheless, the instrument must be divisible and the two instrument halves must be fully movable independently of one another.

The current must here flow from one instrument half including the electrodes incorporated in the branch via the clamped tissue to the counter electrode, which is located in the branch of the other instrument half. In order to allow sealing of different tissue thicknesses, contacting of the two instrument halves must moreover be possible even in the case of different electrode gaps of e.g. 0.1 mm to 1.5 mm.

For achieving an optimum sealing result under these boundary conditions, the target tissue must be present in a strongly compressed state in the area of the above-mentioned electrode gaps, and this can only be guaranteed when the instrument is fully closed via a closing lever that is specially provided for this purpose. Therefore, three positions of the sealing instrument that is adapted to be used for executing an enteroanastomosis are differentiated:

Open, and instrument halves (including branches) separated from one another: at this position both instrument halves can be moved fully freely in space independently of one another. In particular, the two instrument halves can, as is also necessary for executing an anastomosis, be introduced independently of one another in tissue volumes, such as in incisions made into the intestine.

Open, and instrument halves (including branches) connected to and articulated on one another, respectively: the two instrument halves are connected to one another via a plug connection/articulated connection at this position. The two instrument halves can therefore be moved about a common axis of rotation. The tissue can, at this position, still be displaced between the (spaced) branches. At this open position, an RF activation would therefore lead to an uncontrollable fusion result, since the contact pressure required for the fusion processes at the points of contact between the electrodes and the tissue does not exist. Hence, this is a fundamental safety risk that necessitates a safety concept excluding an activation at this position of the instrument.

Closed (tensioned): the instrument has been closed via the above-mentioned internal closing lever and the target tissue has had applied thereto a predefined (minimum) clamping force between the branches and has thus been compressed sufficiently. The target tissue can no longer be displaced between the branches at this position of the instrument. The position of the instrument relative to the tissue can only be changed after renewed opening. This is the only position at which activation of the RF current through the user is allowed.

An RF bipolar sealing instrument of the type in question is known e.g. from U.S. Pat. No. 5,531,744. This instrument consists of two instrument halves which are articulated on one another and which each have provided thereon an electric connection for electrically connecting the respective instrument half to an RF generator. Each instrument half additionally comprises a handle as well as an instrument branch, respectively equipped with at least one electrode. Finally, a bar, which is adapted to be displaced in the longitudinal direction of the handle, is supported on the handle of one instrument half, said bar being coupled with a scalpel that can be extended from the handle along the instrument branch for severing tissue clamped between the instrument branches.

For clamping the tissue with a predetermined clamping force, one of the instrument halves has articulated thereon a closing lever, which has articulated thereon a pawl, as components of the respective handle, such that, when the two instrument halves are manually brought into contact with one another, the pawl can enter into locking engagement with a bolt on the opposite instrument half (opposite handle) so that, by operating the closing lever, a tension force can then be applied to the bolt and, consequently, to the instrument branches abutting on one another (with the tissue located therebetween).

Even if the RF (radio-/high-frequency) sealing instrument according to U.S. Pat. No. 5,531,744 should be demountable into its separate instrument halves, these two instrument halves remain, each via a power supply line of its own, constantly connected to the external RF generator, whereby the individual freedom of movement is limited also in the demounted condition of the instrument. In addition, this known instrument does not provide any protection preventing the instrument branches from having unintentionally applied thereto an RF current at a non-closed position of the instrument branches.

SUMMARY

Taking into consideration the above, it is the object of the present invention to further develop the known RF sealing instrument of the bipolar type such that increased functionality and operational reliability can be achieved. It is a preferred object to provide the possibility of a fully independent manipulation of the two instrument halves. Another preferred object of the present invention is to be seen in allowing a supply of RF current only during the actual fusion process, where applicable adapted to different tissue thicknesses, i.e. at the closed position of the instrument (in the actuated condition of the closing lever /closing mechanism).

These tasks as well as the advantageous objects are solved/achieved by a surgical RF sealing instrument of the bipolar type having features of claim 1 and/or of claim 2. Advantageous further developments of the present invention are the subject matters of the subclaims.

The gist of the invention according to claim 1 therefore is that, in the event that only one of the two instrument halves is connected/adapted to be connected via a power supply line to an energy source, preferably an external RF generator or the like, the power contact between the two instrument halves is configured for electrically coupling said instrument halves in the assembled condition (preferably as a spring contact) for contact closure only at or close to a closure position or a closure position region for different tissue thicknesses, whereas at the open position of the (assembled) instrument the power contact is not closed. In this way, a power current (RF current) is prevented from flowing, in an open position of the instrument, between the electrodes of the two instrument branches through the tissue clamped and compressed therebetween.

The power contact, which is interposed in the RF power supply line, is, as has already been stated, preferably a spring contact, which consequently causes contact closure not only at a single specific closure position of the two instrument branches but also over a predetermined closure position region in accordance with its spring stroke. The instrument can therefore be used for different tissue thicknesses without the necessity of adjusting it to the individual thicknesses.

According to a further aspect of the present invention, which preferably is to be claimed independently, the bipolar RF instrument is equipped with an instrument-internal control switch (not interposed in the RF power current supply line), activated either immediately through/upon assembly of the two instrument halves or, alternatively thereto, only when the predetermined closing force has been reached, so as to enable the supply of electric current from an energy source, preferably an external RF generator, to the two instrument branches. According to another preferred embodiment, the control switch is interposed in the control line between a manual switch or a foot switch and an external energy source, or transmits parallel thereto an electric signal to a (possibly external) control circuit controlling the generation/provision of an RF electric current, i.e. the control switch according to the present invention is preferably not interposed in the power current to the electrodes, but has a blocking or enabling influence preferably on the electric control of the energy source. Even in the event that the one instrument branch which is fundamentally connected to the energy source, or the electrodes embedded in said instrument branch, should, intentionally or unintentionally, be in electric contact with the energy source also in the open position, a manual operation of a manual switch or a foot switch for supplying an RF current to the electrodes would remain ineffective until the (possibly additional) control switch has been closed.

Each of the two above mentioned measures, viz. the arrangement of the power contact and/or of the control switch, are intended to prevent uncontrolled thermofusion in the event that the instrument is open or in the event of freely movable instrument halves (non-assembled condition). Since the two above mentioned measures act on different mechanisms of the instrument, i.e. the power contact is interposed in the power current supply line, whereas the control switch establishes/interrupts the connection between the manual switch or the foot switch and the control circuit, or transmits, alternatively thereto, a (parallel) control signal to the energy source control unit, these two components can be installed in an RF sealing instrument of the type in question independently of one another or in common. In the latter case an additional "fail-safe" effect can be achieved.

According to a further, possibly independent aspect of the present invention, the control switch is interposed in an electric control or signal line between a manual switch or a foot switch and the control unit of preferably the energy source and is thus in a logic AND circuit with the manual switch or the foot switch for closing, at the closure position of the instrument, by means of the manual switch or the foot switch the control line so as to enable the (subsequently executed) selective supply of RF current to the electrodes. This means that a manual operation of the manual switch or the foot switch for supplying current to the electrodes embedded in the instrument branches will not succeed until the control line has been closed by the control switch or, alternatively thereto, a respective (parallel) enabling signal from the control switch is applied to the control unit.

According to a preferred embodiment, the control switch or a key element for operating the control switch is, to this end, mechanically coupled to the closing mechanism (closing lever) of one of the handle units or is operated by the same such that, when the closure position (closure position region), or a position which is located adjacent thereto and at which a predetermined clamping force will presumably be produced via the closing lever, is reached, the control switch is mechanically closed and the respective current enabling signal is generated. Only now is it possible to supply current to the electrodes of the instrument by operating the manual switch or the foot switch.

BRIEF DESCRIPTION OF THE DRAWING FIGURES

The present invention is explained in more detail hereinbelow on the basis of a preferred embodiment making reference to the accompanying figures.

DETAILED DESCRIPTION

Figure 1:
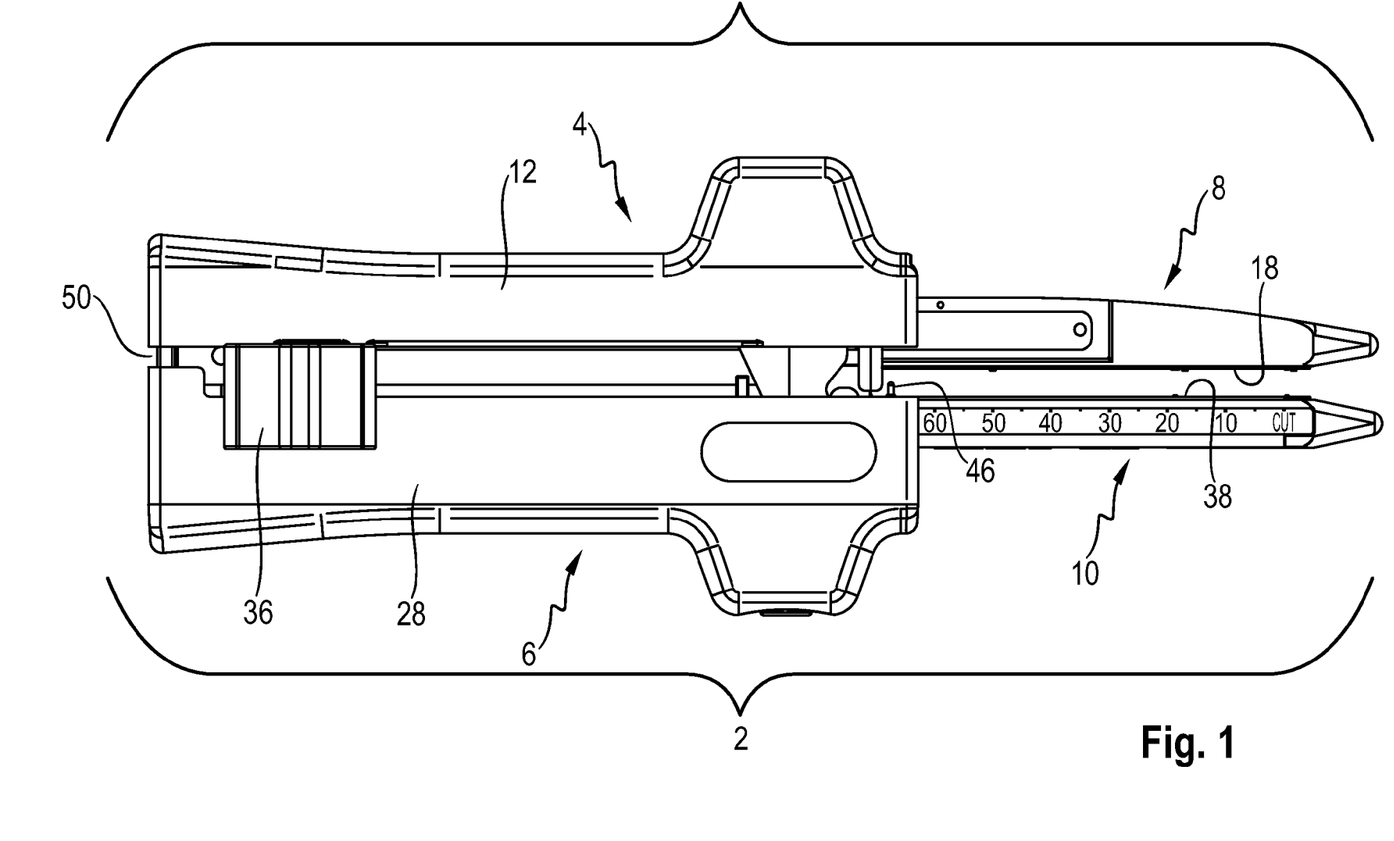
FIG. 1 shows a side view of an RF sealing instrument according to a preferred embodiment of the present invention.

The RF sealing instrument of the bipolar type according to a preferred embodiment of the present invention shown in a side view in FIG. 1 fundamentally comprises two instrument halves 1, 2, which are releasably articulated on one another (adapted to be releasably articulated on one another) and which each consist of a respective handle unit 4, 6 and of an instrument branch 8, 10 arranged distally thereto in the longitudinal direction of the instrument.

Figure 2:
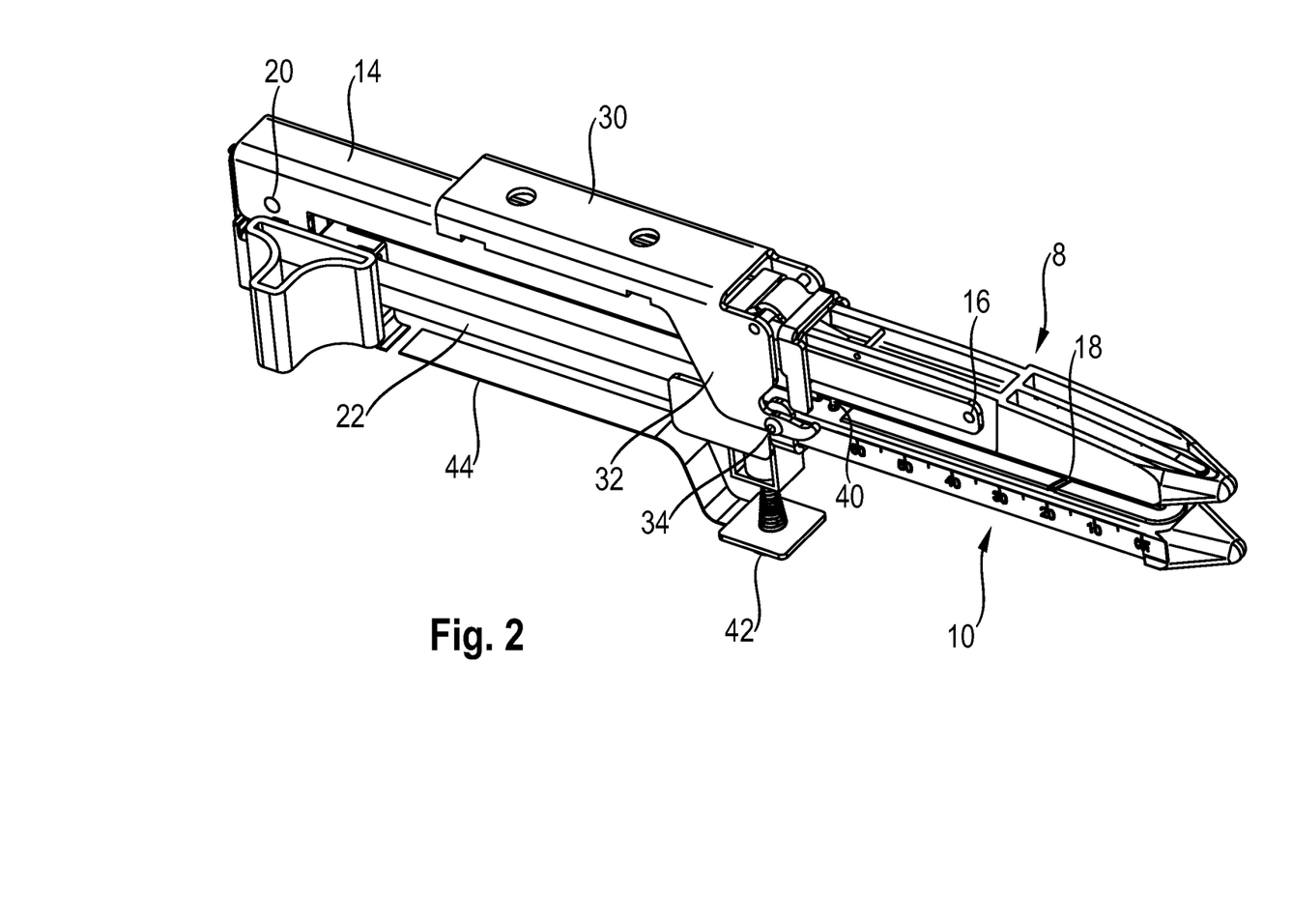
FIG. 2 shows a first perspective view of the RF sealing instrument with out handle shells, from an oblique lateral direction.

The handle unit 4 of the first instrument half 1 constituting the upper instrument half according to FIG. 1 includes an ergonomically shaped handle shell 12 made e.g. of a plastic material or sheet metal material, which, according to FIG. 2, is attached to an axial extension shaft 14 of the instrument branch 8 of said first instrument half 1 such that it protectively covers the same. Below the handle shell 12, the extension shaft 14 of the first (upper) instrument branch 8 according to FIG. 2 has arranged thereon a closing lever 30 whose distal end is supported on the extension shaft 14 such that the lever 30 is pivotable relative to the handle shell 12, said closing lever 30 having additionally an engaging pawl 32 (formed integrally with the closing lever) projecting laterally of the extension shaft 14 in the direction of the other instrument half 2 (constituting the lower instrument half according to FIG. 2). The closing lever 30 including the pawl 32 represents part of an instrument closing mechanism, as will be described in the following.

The extension shaft 14 of the first instrument branch 8 (constituting the upper instrument branch according to FIG. 2) has on its distal end a transversely extending throughhole 16 having a pivot pin (only indicated) inserted therein, the (upper) instrument branch 8 being articulated on said pivot pin like a seesaw, i.e. centrally. At least one, preferably a plurality of electrodes 18 (only schematically indicated in FIG. 2) is embedded in a (lower) longitudinal side of the first (upper) instrument branch 8 facing the opposed second (lower) instrument branch 10, said electrode(s) being connected via an electric power current line, which is not shown in detail, to a contact plate (not shown in detail) arranged on the proximal end portion of the first (upper) instrument branch 8 and exposed in the direction of the (lower) second instrument branch 10.

Figure 3:
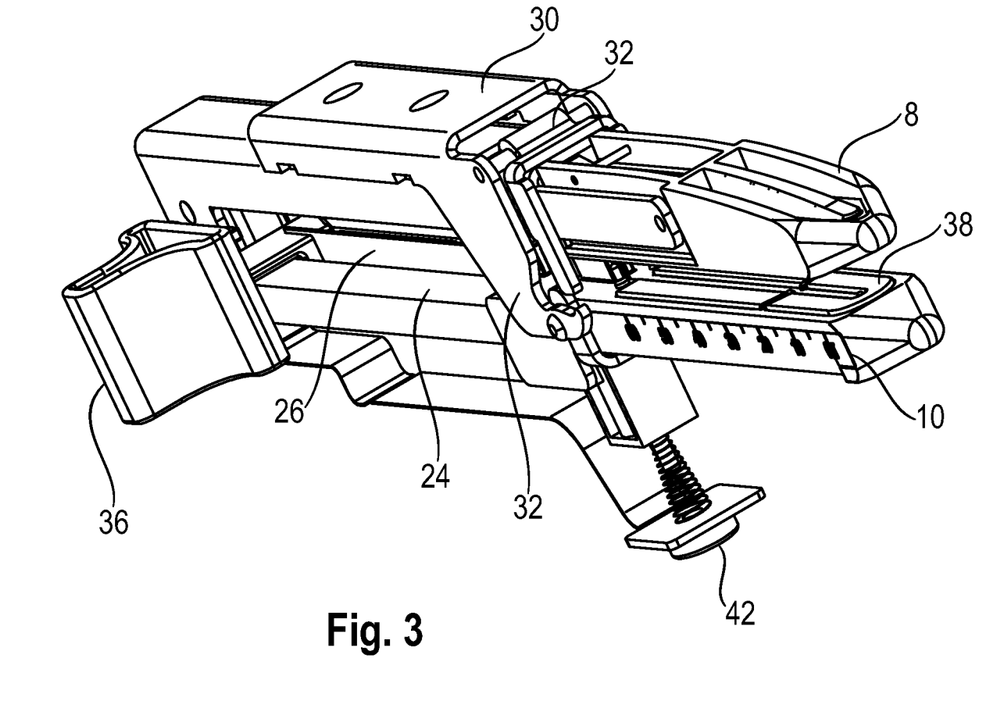
FIG. 3 shows a second perspective view of the RF sealing instrument with out handle shells, from an oblique distal direction.

As can also be seen from FIG. 2, the first (upper) instrument half 1 includes in the proximal area of its handle unit 4 or extension shaft 14 another transverse through-hole having inserted therein a hinge pin 20 onto which the second (lower) instrument half 2 is hinged/is adapted to be hinged. Also this second (lower) instrument half 2 has the distal instrument branch 10 with a proximally extending extension shaft 22 defining, according to FIG. 3 or 4, a longitudinal slot-shaped slide reception means 24 for an axially displaceable cutting/severing knife 26. The (according to FIG. 2 lower) extension shaft 22 also has provided thereon the (lower) handle unit 6 consisting of a handle shell 28 surrounding the (according to FIG. 1 lower) extension shaft 22 and of a locking element 34, with which the engaging pawl 32 of the (upper) closing lever 30 of the first (upper) instrument half 1 can be brought into tensioning engagement so as to pretension the two instrument halves 1, 2 and in particular the two instrument branches 8, 10 relative to one another with a predetermined clamping force.

The severing knife 26 is additionally adapted to be axially displaced from a parking position within the handle shell 28 shown in FIG. 1 to a cutting position in the area of instrument branch 10 by means of a bar 36 projecting laterally from the (lower) handle shell 28. To this end, the severing knife 26 can be configured as a purely mechanically acting scalpel or as an electrically cutting severing plate which, when displaced from its parking position, severs tissue clamped between the instrument branches.

The other (lower) instrument branch 10 is also equipped with at least one electrode or a plurality of electrode segments 38 on its longitudinal side facing the first (upper) instrument branch 8, said electrode or electrode segments 38 being electrically connected to an electric terminal (not shown in detail) via a power current line. This electric terminal, which is preferably arranged on the proximal end of the other (lower) instrument half 2, has connected thereto or is adapted to have connected thereto an energy source, e.g. an RF generator, which is not shown in detail either, so as to apply an RF current to the electrode 38 of the other (lower) instrument half 2 by operating a manual switch 42. In the present embodiment, the manual switch 42 is integrated in the handle unit 6 of the other (lower) instrument half 2 (cf. in this respect in particular FIG. 1). Alternatively, the manual switch may, however, be replaced by an external foot switch. In this case, the manual switch 42 shown in the figures may e.g. be converted into the electric terminal. In both cases the manual switch 42 or the foot switch 42 is connected via a control line 44 to the electronic control of the energy source so as to activate the latter as required.

In addition, starting from the electric terminal, a second electric power current line (not shown) is installed in the other (lower) instrument half 2, said second electric power current line terminating in a power contact 40 arranged at the proximal end of the (lower) instrument branch 10 on the upper longitudinal side thereof.

This power contact 40 consists here of a contact pin 46 (that may also be a flexible tongue or a similar spring contact), which is spring mounted on the proximal end portion of the (lower) instrument branch 10 and which, during closing of the instrument, i.e. when the two instrument branches 8, 10 are moved towards one another, comes into electric contact with the (upper) exposed contact area from a specific relative pivoted position onwards, whereby the (upper) electrode(s) 18 is/are connected to the electric terminal on the other (lower) instrument half 2.

To this end, the contact 46 is supported such that it is able to carry out a specific stroke so that it will already be in electrically conductive contact with the (upper) contact area before the instrument has reached its maximum possible closure/pivoting position, i.e. the electric power contact 40 is closed over a specific pivoting/closure region (referred to as closure position region in the following) of the two instrument branches 8, 10. The only position at which the power contact 40 is definitely not closed is the open position of the instrument. Preferably, the contact pin 46 has a spring stroke allowing a closure position region of the two instrument branches 8, 10 (distance between branches at the closure position) of between 0.1 mm and 1.5 mm gap width between the branches 8, 10. Alternatively, the power contact 40 may, however, also be configured such that it is electrically closed at (or directly before) only a single closure position of the two instrument branches 8, 10.

Figure 4:
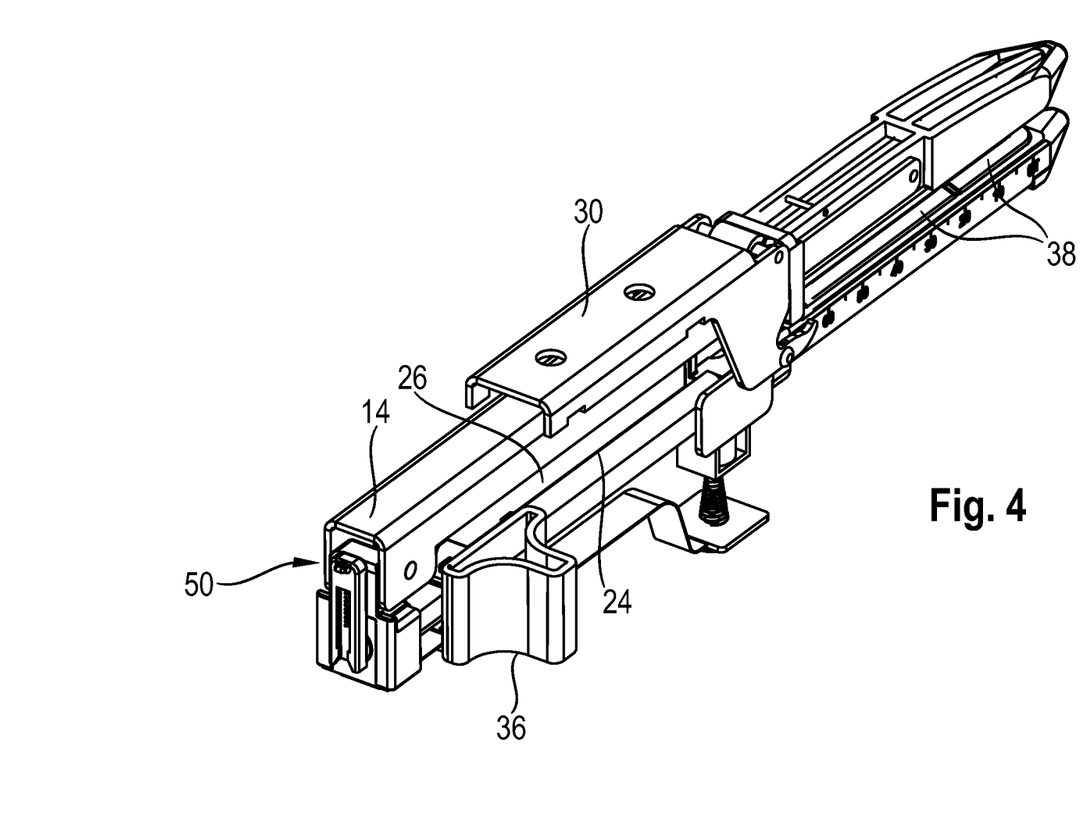
FIG. 4 shows a third perspective view of the RF sealing instrument with out handle shells, from an oblique proximal direction.
Figure 5:
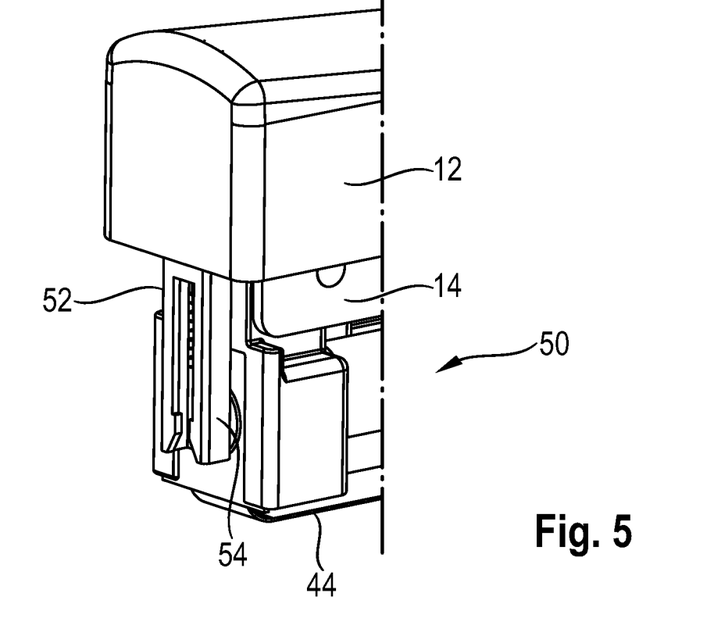
FIG. 5 shows the perspective view of the proximal end portion of the RF sealing instrument in an enlarged representation.
Figure 6:
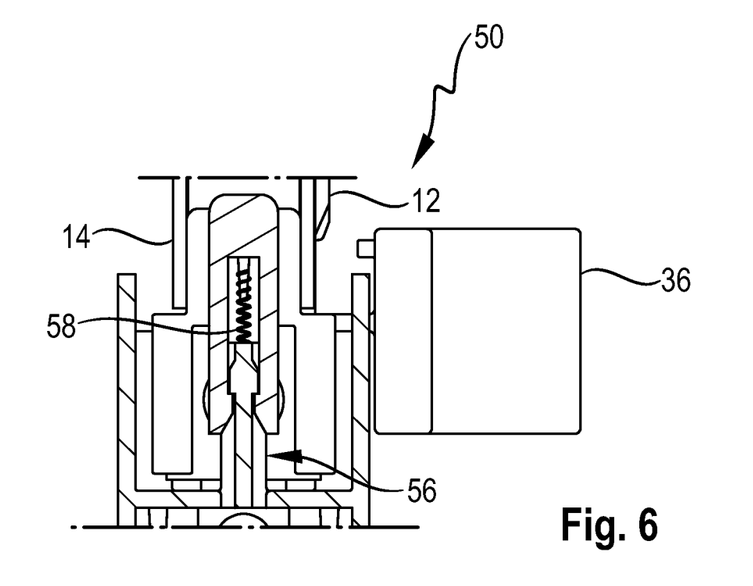
FIG. 6 shows a rear view of the proximal end portion of the RF sealing instrument in an enlarged representation.

In addition to or alternatively to the above described power contact 40 connecting the (upper) electrode(s) 18 to the terminal of the first (upper) instrument half, said first (upper) instrument half 1 has arranged thereon, preferably on the proximal end of the handle unit 4, a further control switch 50 of the type shown especially in FIGS. 4 to 6. This control switch 50 (closure monitoring switch) serves, in principle, to detect the instrument at the open position (according to all the figures) and at the closed position. The (shown) open position serves the purpose of manipulation and grasping the tissue with the instrument. At this position, the tissue is therefore located between the two instrument branches 8, 10 in a non-compressed or non-sufficiently compressed condition. An activation of the RF current at this position may therefore lead to an undesired (incomplete) fusion result and constitutes thus an enormous safety risk for the patient. Complete sealing (fusion) can only take place when the tissue parts to be connected are compressed to a specific extent. In the case of the instrument according to the present invention, this compression is accomplished by applying the above-mentioned minimum clamping force when the instrument is being closed or when the closed position has been reached. It must therefore be guaranteed that this closed position has actually been reached before an RF current is applied to the electrodes 18, 38. This is precisely the purpose for which the control switch 50 is provided in the present embodiment, said control switch 50 being activated via a key element 52 through an operation of the closing lever 30 of the closing mechanism used, when the closed position is reached.

At this point, reference should be made to the fact that the control switch 50 is thus used for the same purpose as the above described power switch 40, but is arranged at a different functional location of the instrument (viz. in the control unit), whereas the power switch 40 is interposed in the power current line. Alternatively, the control switch 50 and its key element 52, respectively, may therefore also be positioned such that it is already operated when the two instrument halves 1, 2 are hinged on one another. In this case, its function would only be to prevent a supply of current to at least the electrode(s) 38 (which could in this case unintentionally act as a monopolar electrode) of the instrument half 2 including the electric terminal until the fully mounted, ready-to-operate condition of the instrument has been established.

Preferably, it is, however, such that the control switch 50 serves to monitor the closure position of the closing lever 30. Only this monitoring allows conclusions to be drawn with respect to a sufficient compression of the tissue and consequently a sufficient contact pressure. The power switch 40, however, only monitors the position of the branches 8, 10.

More concretely, the control switch 50 according to the present invention is a membrane switch mounted at the proximal end of the first (upper) instrument half 1 on the extension shaft 14 thereof, such that its operating field 54 is oriented in the axial direction of the extension shaft 14. At a proximal distance to the operating field 54 of the membrane switch 50 the key element 52 is arranged in the form of a linear slide supported in a transversely displaceable manner on the first (upper) instrument half 1, said linear slide being positioned on a bar-shaped linear guide means 56 on the other (lower) instrument half 2 in sliding engagement therewith and being in operative engagement with or being adapted to be brought into operative engagement with the closing lever 30 (preferably via the upper handle shell 12). More concretely, the proximal end of the upper extension shaft has formed thereon a cross web or cross bar 56 extending in the direction of the other (lower) instrument half 2 and having the bar-shaped key element 52 displaceably arranged thereon. The key element 52 is additionally biased by means of a spring 58 in a direction in which the control switch 50 is not activated. The key element side facing the operating field 54 has formed thereon a projection, which is not shown in detail and which, when the key element 52 is displaced against the force of the spring 58, presses against the operating field 54 thus activating the control switch 50.

This means that, when the closing lever 30 is manually operated via the upper handle shell 12 for clamping tissue between the two instrument branches 8, 10 with a specific clamping force and when it reaches its closure position (corresponds to the closure position at which the predetermined clamping force is obtained), the linear slide 52 is displaced by the closing lever 30 and the upper handle shell 12, respectively, towards the lower instrument half 2, whereupon it presses against the operating field 54 and thus finally closes the electric contact of the control switch (membrane switch) 50.

This has the effect that the control line 44, which extends between the manual switch 42 and the control unit of the energy source and which is routed via control switch 50, is closed, so that an activating signal, which is manually generated at the manual switch 42 and which activates the supply of energy to the electrode(s), can be transmitted via the control switch 50 to the energy source. Alternatively, an electrical signal may, however, be outputted by the control switch 50, when the latter is operated by the key element 52, said electrical signal being applied to an external energy source control circuit, which is not shown in detail and which fundamentally enables the RF current in response to said signal. Only now is it possible to selectively summon the RF current by operating the manual switch or the foot switch and to supply energy to the electrodes for the purpose of thermofusion. In this case, the control circuit 50 would be connected to the energy source control unit parallel to the manual switch or the foot switch.

The advantages of the present invention can therefore be summarized as follows:
  The instrument can be electrically activated neither when the two instrument halves 1, 2 occupy the separated position nor when they occupy the position at which they have already been connected but are still open. This will avoid unintentional, mistimed activation or undefined sealing in a condition in which the tissue is not sufficiently compressed.

For the purpose of triggering, the instrument must be closed and the RF current must be summoned actively by the user via the manual switch 42 or the foot switch 42. This means that, in the embodiment shown, the control switch 50 is in a logic AND circuit with the manual switch or the foot switch 42 for RF activation, so that an RF activation will only take place when both switches have been operated.

The power switch 40 and the control switch 50 operate at different operating locations of the instrument. In particular, the power switch is interposed in the power circuit, whereas the control switch 50 is adapted to be connected to the control of the energy source. Hence, both switches cause, in different ways, a blocking of the supply of current to the electrodes 18, 38 in the event that the instrument is not at its closed position (power switch 40) or does not generate a sufficiently high compression force (control switch 50). Therefore, the two switches can, independently of one another, be installed selectively. If, however, both said switches are installed, a "fail-safe" function is additionally achieved.

Finally, it should also be pointed out that the control switch 50 can be configured such that it has an additional operating field (or an additional control switch may be provided), which is adapted to be activated by the severing knife 26 or by the operating bar 36 of the latter. In this case, this additional control switch signalizes the parking position of the severing knife as a further prerequisite that has to be fulfilled for allowing RF current for the electrodes to be summoned.

Hence, the present invention discloses a surgical RF sealing instrument of the bipolar type, comprising two electrode-equipped, elongate instrument branches 8, 10, which are supported or are adapted to be supported such that they are movable relative to one another (in a hingelike fashion) so as to be operated for moving at least to an open and a closed position, and an instrument handle with two handle units 4, 6, which are associated with the respective instrument branch 8, 10 and which are coupled to one another/adapted to be coupled to one another for manually operating the instrument branches 8, 10 and for applying to the instrument branches 8, 10 a predetermined closing force at the closed position, only one of the two instrument branches 10 having arranged thereon on a terminal for an external energy source (RF generator) and the other instrument branch 8 being adapted to be electrically coupled via an instrument-internal power contact 40 with the instrument branch 10 including the terminal. According to the present invention, the power contact 40 is preferably configured as a spring contact for contact closure only at or close to a closure position (or a closure position region) of the instrument so as to interrupt the contact at an open position of the instrument. In addition to or alternatively to the above, an instrument-internal control switch 50 (on the instrument) is provided, which is only activated when, or a short time before the predetermined closing force (corresponds to the arrival at the closure position/closure position region) is reached, so as to enable the supply of electric current from an external energy source (RF generator) to the instrument branch(es).

What is claimed is:

1. A bipolar radiofrequency (RF) instrument, comprising two instrument halves, each of the two instrument halves comprising an elongate instrument branch comprising one or more electrodes, wherein the elongate instrument branches are supported or are adapted to be supported such that they are movable relative to one another so as to be operated for moving to an open and a closed position, each of the two instrument halves also comprising a handle unit, each elongate instrument branch having associated therewith one of the handle units for manual operation of the elongate instrument branches and for applying to the elongate instrument branches a predetermined closing force at the closed position, and further comprising an instrument-internal control switch located on most ends of the handle units opposite and away from the elongate instrument branches, where the surface lies in a plane that is perpendicular to a plane of tissue contacting surfaces of the one or more electrodes, the instrument-internal control switch automatically activated as a mounting monitor due to a fully mounted and ready-to-operate state of the two instrument halves so as to enable a supply of electric current from an external energy source to the two elongate instrument branches.

2. The bipolar radiofrequency (RF) instrument according to claim 1, wherein a terminal for the external energy source is active on only one of the two elongate instrument branches and another of the two elongate instrument branches is electrically coupled or adapted to be electrically coupled via an instrument-internal power contact with the elongate instrument branch including the terminal, wherein the instrument-internal power contact is preferably configured for contact closure during a closing movement only when the closed position or a closed position region predetermined for different tissue thicknesses is reached, or shortly before that, but is not closed when in the open position of the bipolar radiofrequency (RF) instrument.

3. The bipolar radiofrequency (RF) instrument according to claim 2, wherein the instrument-internal power contact is a spring contact.

4. The bipolar radiofrequency (RF) instrument according to claim 3, wherein the spring contact is a spring-loaded contact pin or a flexible tongue extending from one of the two instrument halves in a direction of another of the two instrument halves so that it can be operated by the said another of the two instrument halves.

5. The bipolar radiofrequency (RF) instrument according to claim 3, wherein the instrument-internal power contact is arranged in an area of the elongate instrument branches outside tissue clamping portions thereof.

6. The bipolar radiofrequency (RF) instrument according to claim 3, wherein the spring contact is configured or arranged on the bipolar radiofrequency (RF) instrument such that it causes contact closure resiliently over a predetermined closure position or a predetermined motion range of the elongate instrument branches in accordance with a spring stroke.

7. The bipolar radiofrequency (RF) instrument according to claim 6, wherein, after the contact closure over the predetermined closure position or the predetermined motion range, two contact elements, which are adapted to be moved into electric contact with one another, are adapted to be held such that they are not movable relative to one another.

8. The bipolar radiofrequency (RF) instrument according to claim 7, wherein the spring contact is configured or arranged on the bipolar radiofrequency (RF) instrument such that the contact closure is established in a middle region of the predetermined closure position or the predetermined motion range of the elongate instrument branches and is then maintained until a maximum closure position has been reached.

9. The bipolar radiofrequency (RF) instrument according to claim 1, wherein the instrument-internal control switch is a key switch, arranged on one of the two instrument halves and operable by a key element on said one instrument half of the two instrument halves.

10. The bipolar radiofrequency (RF) instrument according to claim 9, wherein the instrument-internal control switch is positioned on the handle unit of said one instrument half of the two instrument halves.

11. The bipolar radiofrequency (RF) instrument according to claim 10, wherein the instrument-internal control switch is connected to a control unit of the external energy source via an electric line so as to transmit, by means of an additional manual switch or foot switch, a mounting-finished signal to the control unit of the external energy source for selectively applying a radiofrequency (RF) current to the one or more electrodes.

12. The bipolar radiofrequency (RF) instrument according to claim 10, wherein the instrument-internal control switch is interposed in a control line between a manual switch or a foot switch and a control unit of the external energy source.

\* \* \* \* \*